(12) United States Patent
Brace

(10) Patent No.: US 6,338,338 B1
(45) Date of Patent: Jan. 15, 2002

(54) INHALATION APPARATUS

(75) Inventor: Geoff Brace, Raleigh, NC (US)

(73) Assignee: Bespak PLC, Norfolk (GB)

( * ) Notice: Subject to any disclaimer, the term of this patent is extended or adjusted under 35 U.S.C. 154(b) by 0 days.

(21) Appl. No.: 09/380,707

(22) PCT Filed: Mar. 13, 1998

(86) PCT No.: PCT/GB98/00758
§ 371 Date: Dec. 8, 1999
§ 102(e) Date: Dec. 8, 1999

(87) PCT Pub. No.: WO98/41252
PCT Pub. Date: Sep. 24, 1998

(30) Foreign Application Priority Data

Mar. 14, 1997 (GB) ............................................. 9705388

(51) Int. Cl.[7] .............................................. A61M 11/00
(52) U.S. Cl. ............................ 128/200.23; 128/200.14; 128/200.22
(58) Field of Search ........................ 128/200.14, 200.18, 128/200.19, 200.21, 200.22, 200.23, 203.15

(56) References Cited

U.S. PATENT DOCUMENTS 3,184,115 A * 5/1965 Meshberg .................... 222/156
4,834,083 A * 5/1989 Byram et al. ........... 128/200.23
4,969,578 A * 11/1990 Gander et al. ............... 222/131
5,460,171 A   10/1995 Pesenti et al.
5,598,836 A    2/1997 Larson et al.
6,065,471 A *  5/2000 Schaeffer et al. ....... 128/203.15

FOREIGN PATENT DOCUMENTS

| FR | 0 414 536 a2 | * | 8/1990 |
| GB | 2 061 116 | | 5/1981 |
| WO | WO92 04070 | | 3/1992 |
| WO | WO93 09830 | | 5/1993 |

* cited by examiner

Primary Examiner—John G. Weiss
Assistant Examiner—V. Srivastava
(74) Attorney, Agent, or Firm—Smith, Gambrell & Russell, LLP

(57) ABSTRACT

An inhalation apparatus for dispensing a product that includes a housing and an end cap axially slidable relative to the housing. The housing has a portion adapted to receive a pressurized dispensing container and connected to a mouthpiece, and duct means communicating with the container-receiving portion for conveyance of product toward the mouthpiece. The end cap has a socket for engaging the pressurized dispensing container. The end cap has a collar with an inwardly directed rim. The housing includes an outwardly directed flange which fits within the rim. The end cap is movable between a first position in which the rim and flange have an axial overlap and there is no or a minimal flow of air through the housing, and a second position in which there is a maximum flow of air, the air flow being created by a user applying suction to the mouthpiece.

11 Claims, 4 Drawing Sheets

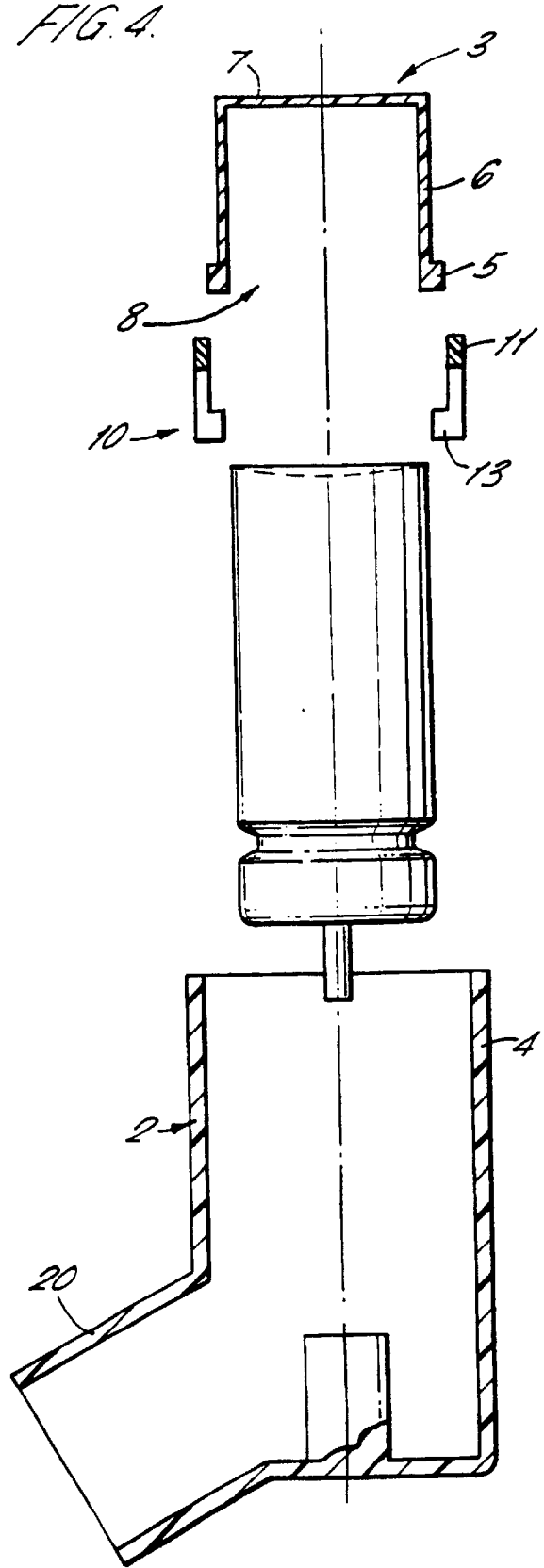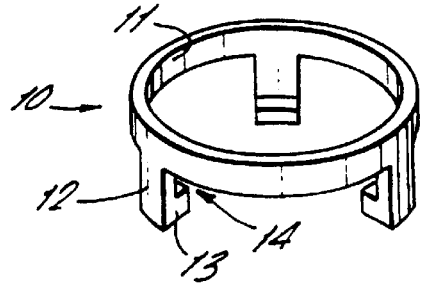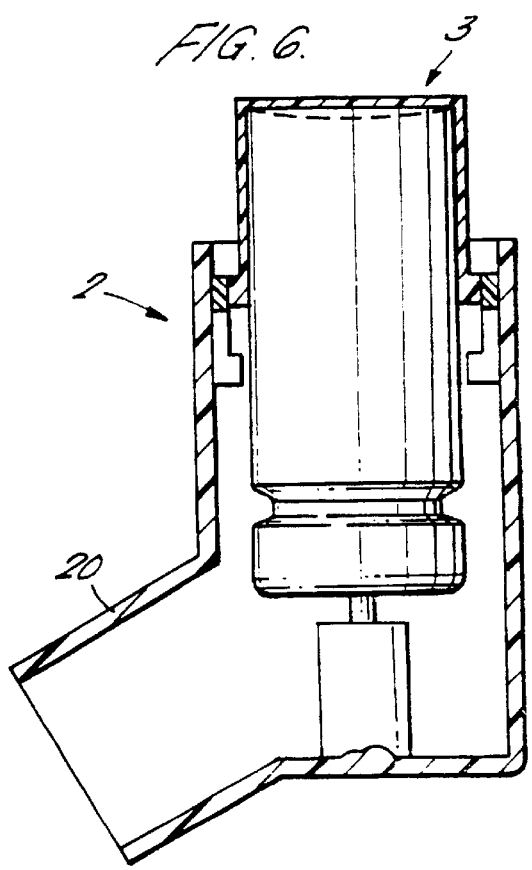

INHALATION APPARATUS

This invention relates to an inhalation apparatus for dispensing substances for inhalation and, in particular, but not exclusively, for dispensing medicinal products in aerosol form from a pressurised dispensing container.

It is known to provide a sensor in an inhalation apparatus to detect inhalation by the user in order to synchronise with inhalation the release into the inhaled air flow of the substance to be inhaled. It is, for example, important in the administration of aerosol products for the relief of asthma that the timing of the dispensing operation should be carefully controlled to ensure maximum deposition of substance in the user's lungs.

It is known from GB 2266466 to provide an electrically operated dispensing means responsive to a signal generated by a sensor which is responsive to a flow of air through the passageway. The disadvantage of this solution is that the apparatus is expensive.

An object of the present invention is to provide dispensing means in which mechanical means are used to co-ordinate the release of the substance with the inhalation.

The present invention therefore provides an inhalation apparatus for dispensing a product comprising a housing and an end cap axially slidable relative to the housing, said housing comprising a position adapted to receive a pressurized dispensing container and being connected to the mouthpiece, and a duct communicating with the container receiving portion for conveyance of product towards the mouthpiece; said end cap comprising a portion for engaging the pressurized dispensing container; one of said end cap and housing comprising an inwardly directed rim; the other of said end cap and housing including an outwardly directed flange which fits within said rim; said end cap being movable between a first position in which said rim and flange have an axial overlap and there is no or a minimal flow of air through said housing and a second position in which there is a maximum flow of air, the air flow being created by a user applying suction to the mouthpiece.

An advantage of the present invention is that the dispensation of the medicament is synchronised with inhalation of the user using an inexpensive inhalation apparatus.

Preferably said end cap is movable to a third position, the movement of the end cap between the second and third position s providing means for the dispensing of the product into the maximum air flow and for delaying the discharge of the product until the maximum air flow has been established.

Preferably the end cap comprises the inwardly directed rim and the housing comprises the outwardly directed flange.

Alternatively the housing comprises the inwardly directed rim and the end cap comprises the outwardly directed flange.

Preferably the end cap comprises a collar comprising the inwardly directed rim and a plurality of axial ribs on an internal surface of the collar, said rim and ribs, with the end cap in the first position, forming a close fit with the outwardly directed flange of the housing so that there is no or a minimum air flow through the housing, an end of the axial ribs furthest from the rim comprising position stops for contacting the rim when the end cap is in the third position to prevent axial movement of the rim beyond the stops; the collar further comprising circumferential recesses between the ribs such that with the end cap in the second or third positions, the maximum air flow can pass through the circumferential recesses between the housing and the collar when a user applies suction to the mouthpiece.

Alternatively the housing comprises a collar comprising the inwardly directed rim and a plurality of axial ribs on an internal surface of the collar, said rim and ribs, with the end cap in the first position, forming a close fit with the outwardly directed flange of the end cap so that there is no or a minimum air flow through the housing, an end of the axial ribs furthest from the rim comprising position stops for contacting the rim when the end cap is in the third position to prevent axial movement of the rim beyond the stops; the collar further comprising circumferential recesses between the ribs such that with the end cap in the second or third positions, the maximum air flow can pass through the circumferential recesses between the housing and the collar when a user applies suction to the mouthpiece.

Preferably the minimum air flow is provided by a bleed hole in the housing.

Alternatively the minimum air flow is provided by a bleed hole in the end cap.

An advantage of providing a bleed hole is that a minimum air flow is provided when suction is applied to the mouthpiece even when the apparatus is in the rest state with the rim and flange having an axial overlap. This prevents the user of the inhalation apparatus panicking by being unable to inhale a quantity of air.

Preferably the ratio of the maximum volume flow rate of air to the minimum volume flow rate of air lies in the range 8 to 12.

Preferably the ratio of the maximum volume flow rate of air to the minimum volume flow rate of air is approximately 10.

Preferably the end cap is biased in use into the first position by means of the pressurised dispensing container.

An advantage of the present invention is that the apparatus does not require a separate spring component in order to operate. This helps to reduce the manufacturing and assembly costs of the apparatus.

Preferred embodiments of the present invention will now be described, by way of example only, with reference to the accompanying drawings of which:

FIG. 4 is an exploded sectional view of a second embodiment of the present invention;

FIG. 5 is a perspective view of a part of the second embodiment of the present invention;

FIG. 6 is a sectional view of a second embodiment of the present invention.

Figure 1:
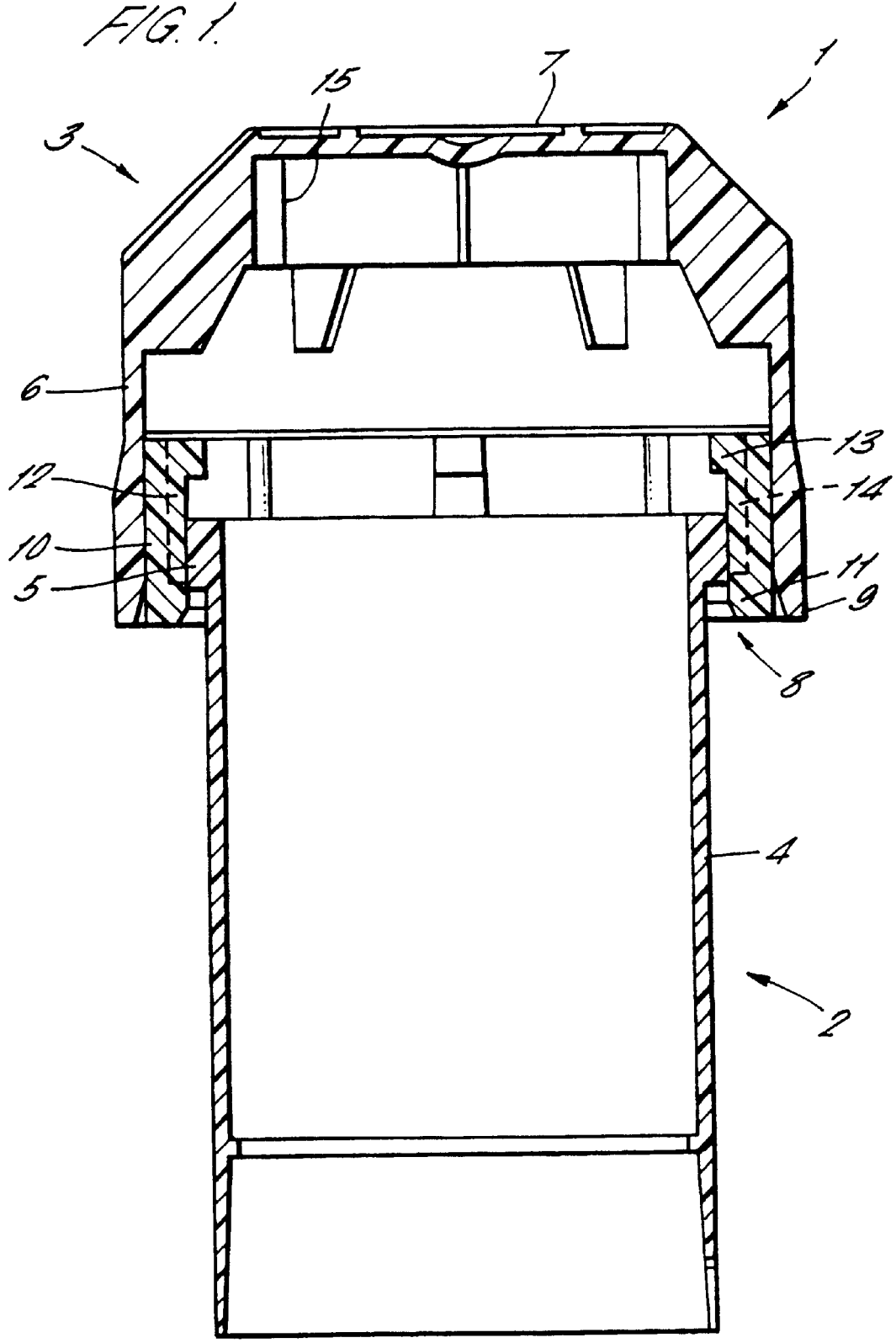
FIG.1 is a sectional view of a part of a first embodiment of the present invention.

Referring to FIG. 1, a first embodiment of the apparatus 1 comprises a housing 2 and end cap 3. The housing 2 comprises a generally cylindrical portion 4 open at both ends. The cylindrical portion 4 has an outwardly directed circumferential flange 5 of enlarged external diameter at one end. The apparatus 1 further includes a mouthpiece incorporating a stem block for receiving in use a valve stem of a pressurized dispensing container (see. for example, mouthpiece 20 and FIGS. 5 and 6 for an illustration of each relative to a different embodiment). The mouthpiece can be coupled to the housing 2 at the end of the housing 2 remote from the circumferential flange by means of a push fit (not shown).

Preferably, however the mouthpiece and the housing 2 are manufactured as a single component, for example, by means of a plastic moulding, as shown in FIG. 5.

Figure 2:
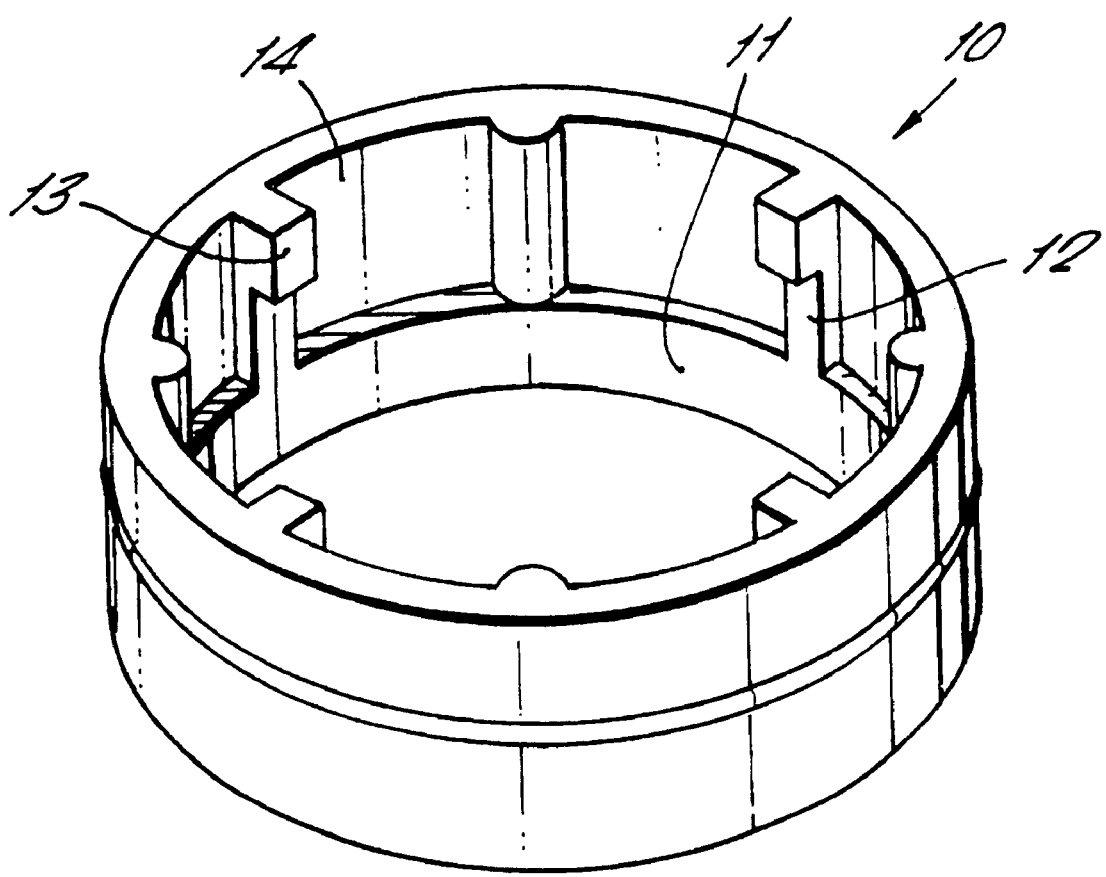
FIG. 2 is a perspective view of a part of the first embodiment of the present invention.

The end cap 3 comprises a generally cylindrical portion 6 closed at one end to form an end face 7. The cylindrical portion 6 of the end cap 3 comprises an open end 8 having a flared circumferential skirt 9. A collar 10, as shown in FIG. 2, is received in the open end 8 of the end cap 3 and is held in the cylindrical portion 6 by means of an interference fit between the external diameter of the collar 10 and the internal diameter of the cylindrical portion 6 of the end cap 3.

The collar 10 comprises an internal rim 11 and axial ribs 12, on the internal surface of the collar, 10 spaced around the circumference of the collar 10. Between the axial ribs 12 are positioned circumferential recesses 14. The external diameter of the circumferential flange 5 of the housing 2 is slidably engagable with the internal surface of the rim 11 and ribs 12 of the collar 10. The external diameter of the circumferential flange 5 forms a close fit with the internal diameter of both the rim 11 and the ribs 12 of the collar 10 sufficient to limit substantially and possibly prevent the flow of air between the rim 11 and circumferential flange 5 when the rim 11 and circumferential flange are axially aligned but which is not sufficient to prevent axial movement of the circumferential flange 5 relative to the collar 10. Position stops 13 are provided on each axial rib 12 on an end of the collar 10 nearest the end face 7 of the end cap 3 to position the collar 10 on first actuation of the apparatus.

Before first use the collar 10 is positioned over the housing 2 with the position stops 13 resting on the distal end of the circumferential flange 5. The end cap 3 is placed over the collar 10. The collar 10 is preferably designed not to be removed from the end cap 3 throughout the working lifetime of the apparatus 1. The pressurised dispensing container is inserted, with the valve stem of the container downwards (as viewed in FIG. 1), into the housing 2. The base of the pressurised dispensing container is received within a socket 15 of the end cap 3 and held in position by means of an interference fit between the socket 15 and container. The apparatus 1 is fully actuated by depressing the end cap 3. This movement forces the collar 10 axially along the end cap 3 by means of the flange 5 of the housing 2 being in contact with the position stops 13 of the collar 10. The collar 10 comes to its rest position where preferably it remains throughout the working life of the inhaler. The rest position of the collar 10 is such that in future operation of the inhaler the flange 5 comes into contact with the position stops 13 at the same time as the valve stem of the dispensing container is fully depressed. Thus the axial movement of the collar 10 relative to the housing 2 is limited by the stroke length of the valve stem of the dispensing container. In the assembled position there exists a gap between the internal surface of the housing 2 and the external surface of the dispensing container which may determine the maximum opening and hence the maximum volume air flow rate through the housing.

A mouthpiece comprising a stem block (not shown in FIGS. 1–3 but of known type) is removably coupled to the end of the housing 2 furthermost from the circumferential flange 5. The valve stem of the pressurized dispensing container is engagable within the stem block of the mouthpiece. Thus when the apparatus 1 is assembled the end cap 3 is axially slidable relative to the housing 2 and mouthpiece; the axial movement of the end cap 3 being limited solely by the stroke length of the valve of the dispensing container. The axial movement is limited at one extreme by the rest position of the dispensing can and at the other extreme by the position of the dispensing container with the valve stem in the fully depressed state.

Figure 3A:
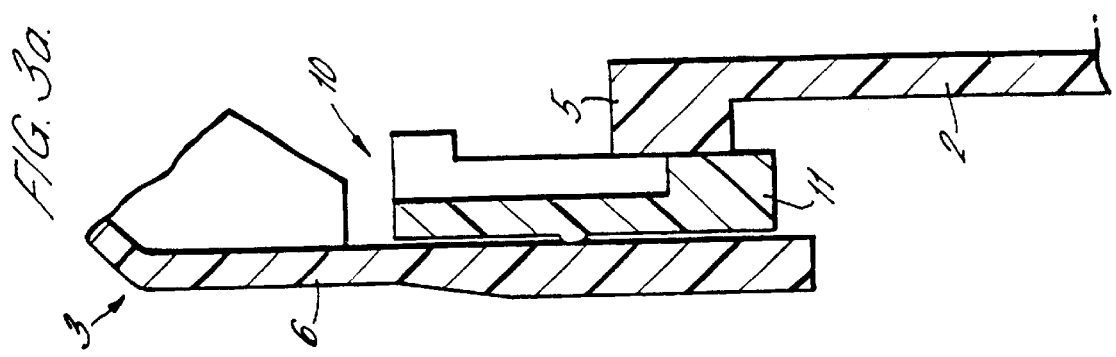
FIG. 3a is a sectional view of a part of the first embodiment of the present invention in a first position.

In a first, rest position of the apparatus, as shown in FIG. 3a, the length of the housing 2 relative to the dispensing container is such that the circumferential flange 5 is at least partially aligned with the raised rim 11 of the collar 10. The fit between the circumferential flange 5 and rim 11 largely prevents the passage of air between the raised rim 11 and circumferential flange 5. Thus, when a user of the inhalation apparatus applies suction to the mouthpiece, no substantial air flow between the rim 11 and circumferential flange 5 is produced. It is to be desired that in the first position with the circumferential flange 5 and rim 11 in alignment there is a minimum volume flow rate of air through the inhaler into the user's mouth when suction is applied to the mouthpiece 7. This minimum flow of air helps to prevent any sense of panic which may occur if the user of the inhaler was not able to inhale a quantity of air. Such a minimum volume flow rate of air may be produced by incorporating a bleed hole in the collar 10. Alternatively, the minimum volume flow rate of air may be ensured by designing the circumferential flange 5 and rim 11 interface to have a minimum leakage of air whilst in the first position or incorporating a bleed hole in another portion of the housing or end cap 2, 3. Thus, the inhaler has a minimum volume flow rate of air through the inhaler with the housing 2 in a first position corresponding to non-actuation of the apparatus 1. The ratio of the maximum to minimum volume flow rates may be varied greatly, and may be easily adjusted by altering the size of the bleed hole and/or the nature of the sealing contact of the rim 11 with the circumferential flange 5. Preferably, the ratio of the maximum to minimum volume flow rates of air lies in the range of 8 to 12 and preferably the ratio of maximum to minimum volume flow rates of air is approximately 10.

Figure 3B:
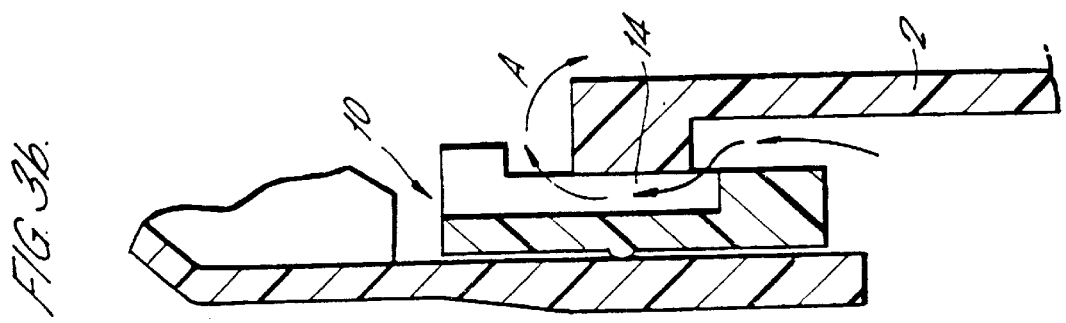
FIG. 3b is a sectional view of a part of the first embodiment of the present invention in a second position.
Figure 3C:
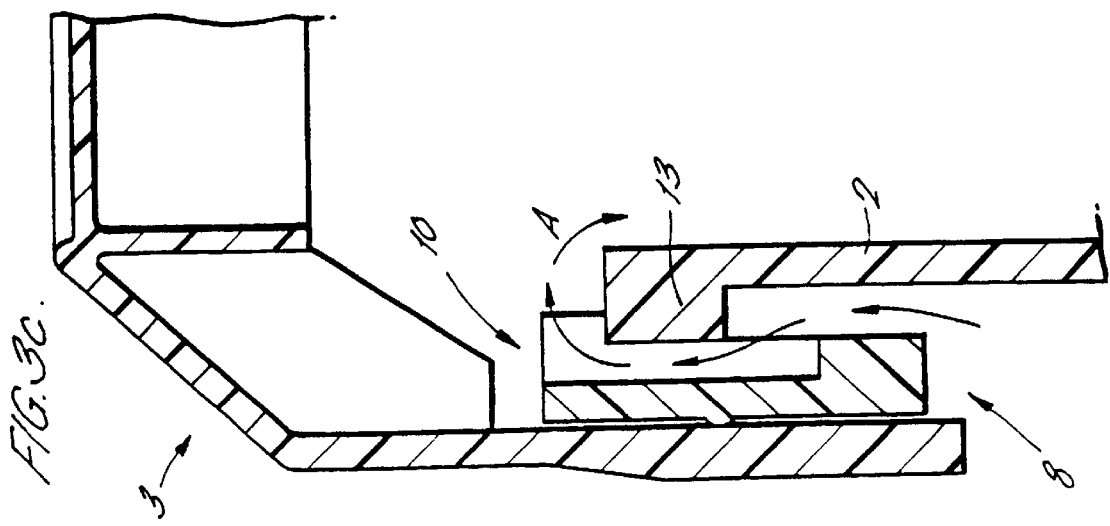
FIG. 3c is a sectional view of a part of the first embodiment of the present invention in a third position.

To actuate the apparatus, the user of the inhaler depresses the end face 7 of the end cap 3. This causes the valve stem of the dispensing container to start to slide and, at the same time, the circumferential flange 5 to slide relative to the collar 10 from a first to a second position, as shown in FIG. 3b, bringing the circumferential flange 5 into axial alignment with the circumferential recesses 14 of the collar 10. In this second position, an air flow path, shown by the arrows marked 'A' in FIGS. 3b and 3c, is created from a position external the inhalation apparatus 1 through the open end 8 of the end cap 3, through the circumferential recesses 14 and into the housing 2. The air then passes between the housing 2 and the dispensing container and into the mouthpiece. This air flow comprises a maximum volume flow rate through the apparatus 1. Continued depression of the end cap 3 moves the housing 2 to a third position, as shown in FIG. 3c, where the circumferential flange 5 contacts the position stops 13, preventing further axial movement of the housing 2. The dispensing container discharges a dose of medicament into the air flow as the end cap 3 moves from the second position to the third position. Alternatively the dispensing container discharges a dose simultaneously with the end cap 3 reaching the third position.

The reliable operation of inhalers, in terms of consistent timing of the discharge of product and full dispensation of each metered dose, has been found to be dependant to a certain extent on the variation in height of the body of the dispensing container, which has been found to vary by up to an amount of the same order as the stroke length of the valve stem.

The present invention overcomes this reliability problem due to the fact that when the apparatus is first assembled the collar 10 is placed in the end cap 3 and the pressurised dispensing container and mouthpiece are coupled to the end cap 3 and the apparatus 1 is actuated by firmly squeezing together the end cap 3 and mouthpiece. This has the effect of moving the collar 10 axially within the end cap 3 to a point where the fully depressed state of the valve stem of the pressurised dispensing container corresponds to the third position of the end cap in which the flange 5 contacts the position stops 13. The collar 10 is held fixed by the tight fit between the collar 10 and end cap 3 when the apparatus 1 is released, thus the apparatus 1 is 'set up' for the individual characteristics of the dispensing container inserted. The reliability of the apparatus 1 is further improved due to the fact that the minimum air flow is ensured even if the flange 5 and rim 11 only partially axially overlap. The length of the cylindrical portion 6 of the end cap 3 allows a degree of axial movement of the collar 10 relative to the dispensing container during the initial 'setting up' of the apparatus 1. The length of the cylindrical portion 6 thus provides a tolerance of several millimetres for the accurate positioning of the collar 10 with the housing 2 in the first position.

The timing of the discharge of the container can be easily varied in relation to the start of the maximum air flow by altering the axial length of the collar 10 or circumferential recesses 14. In particular altering the axial length of the rim 11 and flange 5 will alter the degree of axial movement of the housing 2 that is required to move the rim 11 and flange 5 from the overlapping state to the non-overlapping state and hence from the minimum air flow position to the maximum air flow position.

A second embodiment of the present invention is shown in FIGS. 4 to 6. Features in common with the first embodiment have been designated with like reference numerals.

The apparatus 1 comprises a housing 2 and an end cap 3. The housing 2 comprises a generally cylindrical portion 4 open at both ends. The apparatus 1 further includes a mouthpiece 20 incorporating a stem block with duct (not shown but a conventional feature of a stem block) for receiving in use a valve stem of a pressurised dispensing container. The mouthpiece 20 extends from the end of the housing 2. Preferably the mouthpiece 20 and the housing 2 are manufactured as a single component, for example, by means of plastic moulding.

The end cap 3 comprises a generally cylindrical portion 6 closed at one end to form an end face 7. The cylindrical portion 6 of the end cap 3 comprises an open end 8 having an outwardly directed circumferential flange 5. A collar 10, as shown in FIG. 6, is received in the open end of the housing 2 and is held in the cylindrical portion 4 by means of an interference fit between the external diameter of the collar 10 and the internal diameter of the cylindrical portion 4 of the housing 2.

The collar 10 as shown in FIG. 5 comprises an internal rim 11 and axial ribs 12, on the internal surface of the collar 10, spaced around the circumference of the collar 10. Between the axial ribs 12 are positioned circumferential recesses 14. The external diameter of the circumferential flange 5 of the housing 2 is slidably engagable with the internal surface of the rim 11 and ribs 12 of the collar 10. The external diameter of the circumferential flange 5 forms a close fit with the internal diameter of both the rim 11 and the ribs 14 of the collar 10 sufficient to limit substantially and possibly prevent the flow of air between the rim 11 and circumferential flange 5 when the rim 11 and circumferential flange 5 are axially aligned but which is not sufficient to prevent axial movement of the circumferential flange 5 relative to the collar 10. Position stops 13 are provided on each axial rib 14 on an end of the collar 10 nearest the mouthpiece 20 of the housing 2 to position the collar 10 on first actuation of the apparatus.

Before first use the collar 10 is placed in the housing 2 with the position stops 13 nearest the mouthpiece 20. The pressurised dispensing container is inserted, with the valve stem of the container downwards (as viewed in FIG. 6), into the housing 2 and through the collar 10. The end cap 3 is push fit over the base of the dispensing container such that the flange 5 is positioned within the collar 10. The collar 10 is preferably designed not to be removed from the housing 2 throughout the working lifetime of the apparatus 1. The apparatus 1 is fully actuated by depressing the end cap 3. This movement forces the collar 10 axially along the end cap 3 by means of the flange 5 of the end cap 3 being in contact with the position stops 13 of the collar 10. The collar 10 comes to its rest position where preferably it remains throughout the working life of the inhaler. The rest position of the collar 10 is such that in future operation of the inhaler the flange 5 comes into contact with the position stops 13 at the same time as the valve stem of the dispensing container is fully depressed. Thus the axial movement of the collar 10 relative to the housing 2 is limited by the stroke length of the valve stem of the dispensing container. In the assembled position there exists a gap between the internal surface of the housing 2 and the external surface of the dispensing container which may determine the maximum opening and hence the maximum volume air flow rate through the housing.

Operation of the second embodiment of the present invention is similar to the first embodiment; movement of the end cap 3 between the first, second and third positions actuating the apparatus 1 and controlling the flow of air when a user applies suction to the mouthpiece 20.

All of the components of the apparatus 1 can be plastic mouldings.

It will be appreciated that various modifications to the construction of the apparatus 1 may be made without departing from the scope of the invention.

What is claimed is:

1. An inhalation apparatus for dispensing a product comprising a housing, an end cap seated axially slidable relative to the housing and a collar in one or other of the end cap, or housing, said housing comprising a portion adapted to receive a pressurised dispensing container and being connected to a mouthpiece, and a duct communicating with the container receiving portion for conveyance of product towards the mouthpiece; said end cap comprising a portion for engaging a pressurised dispensing container; said collar comprising an inwardly directed rim; one of said end cap and said housing including an outwardly directed flange which fits within said rim; said end cap being movable from a first position in which said rim and flange have an axial overlap and there is no or a minimal flow of air through said housing to a second position in which there is a maximum flow of air, the air flow being created by a user applying suction to the mouthpiece, wherein the collar is slidably moveable relative to its seat in the end cap or housing on a first actuation of the inhalation apparatus to axially position the collar relative to the end cap or housing to accommodate variations in the axial length of the valve stem of a pressurised dispensing container received, in use, in the housing.

2. An inhalation apparatus as claimed in claim 1, wherein said end cap is movable to a third position, the movement of the end cap between the second and third positions providing means for the dispensing of the product into the maximum air flow and for delaying the discharge of the product until the maximum air flow has been established.

3. An inhalation apparatus as claimed in claim 1, wherein the collar is seated in the end cap and the housing comprises the outwardly directed flange.

4. An inhalation apparatus as claimed in claim 1, wherein the collar is sated in the housing and the end cap comprises the outwardly directed flange.

5. An inhalation apparatus as claimed in claim 3, wherein the collar comprises a plurality of axial ribs on an internal surface of the collar, the rim and ribs, with the end cap in the first position, forming a close fit with the outwardly directed flange so that there is no or a minimum air flow through the housing, an end of the axial ribs furthest from the rim comprising position stops for contacting the rim when the end cap is in the third position; the collar further comprising circumferential recesses between the ribs such that with the end cap in the second or third positions, the maximum air flow can pass through the circumferential recesses between the housing and the collar when a user applies suction to the mouthpiece.

6. An inhalation apparatus as claimed in claim 4, wherein the collar comprises a plurality of axial ribs on an internal surface of the collar, the rim and ribs, with the end cap in the first position, forming a close fit with the outwardly directed flange so that there is no or a minimum air flow through the housing, an end of the axial ribs furthest from the rim comprising position stops for contacting the rim when the end cap is in the third position; the collar further comprising circumferential recesses between the ribs such that with the end cap in the second or third positions, the maximum air flow can pass through the circumferential recesses between the housing and the collar when a user applies suction to the mouthpiece.

7. An inhalation apparatus as claimed in claim 1, wherein the minimum air flow is provided by a bleed hole in the housing.

8. An inhalation apparatus as claimed in claim 1, wherein the minimum air flow is provided by a bleed hole in the end cap.

9. An inhalation apparatus as claimed in claim 1, wherein the ratio of the maximum volume flow rate of air to the minimum volume flow rate of air lies in the range 8 to 12.

10. An inhalation apparatus as claimed in claim 1, wherein the ratio of the maximum volume flow rate of air to the minimum volume flow rate of air lies is approximately 10.

11. An inhalation apparatus as claimed in claim 1, wherein the end cap is biased in use into the first position by means of a pressurised dispensing container.

\* \* \* \* \*